US010857313B2

(12) United States Patent
Fink et al.

(10) Patent No.: US 10,857,313 B2
(45) Date of Patent: Dec. 8, 2020

(54) LIQUID NEBULIZATION SYSTEMS AND METHODS

(71) Applicant: Aerami Therapeutics, Inc., Durham, NC (US)

(72) Inventors: Jim Fink, Brisbane, CA (US); Lisa Molloy, Brisbane, CA (US); Ronan MacLoughlin, Craughwell (IE); Claire Elizabeth Lillis, Kingston (IE); Michael Joseph Casey, CorrnaMona (IE); John Matthew Mullins, Tuam (IE); Kieran James Hyland, Salthill (IE); Joseph Martin Grehan, Gort (IE); Niall Scott Smith, Alloa (SL)

(73) Assignee: Aerami Therapeutics, Inc., Durham, NC (US)

(*) Notice: Subject to any disclaimer, the term of this patent is extended or adjusted under 35 U.S.C. 154(b) by 1104 days.

(21) Appl. No.: 14/743,711

(22) Filed: Jun. 18, 2015

(65) Prior Publication Data
US 2016/0001019 A1 Jan. 7, 2016

Related U.S. Application Data

(60) Provisional application No. 62/019,781, filed on Jul. 1, 2014.

(51) Int. Cl.
A61M 15/00 (2006.01)
A61M 11/00 (2006.01)
A61M 16/00 (2006.01)

(52) U.S. Cl.
CPC ...... A61M 15/0021 (2014.02); A61M 11/005 (2013.01); A61M 15/002 (2014.02);
(Continued)

(58) Field of Classification Search
CPC ............ A61M 15/0021; A61M 11/005; A61M 15/0085; A61M 2016/0021;
(Continued)

(56) References Cited

U.S. PATENT DOCUMENTS 3,789,843 A 2/1974 Armstrong et al.
4,564,129 A 1/1986 Urban et al.
(Continued)

FOREIGN PATENT DOCUMENTS

EP 2283887 A1 2/2011
EP 2724741 A1 4/2014
(Continued)

OTHER PUBLICATIONS

Partial Supplemental European Search Report dated Feb. 12, 2018 for European Patent Application No. 15814881.4; 9 pages.
(Continued)

Primary Examiner — Timothy A Stanis
Assistant Examiner — Jonathan S Paciorek
(74) Attorney, Agent, or Firm — Kilpatrick Townsend & Stockton LLP

(57) ABSTRACT

Embodiments provide aerosolization device for providing aerosolized medicament to user. The aerosolization device includes conduit, aerosol generator, fluid receiving chamber, restrictor within the conduit, and indicator mechanism. Conduit has an inner wall and a mouthpiece end for causing an inspiratory flow. Aerosol generator includes a vibratable mesh laterally offset from the inner wall. Fluid receiving chamber receives liquid medicament. At least a portion of chamber is tapered such that liquid medicament is directed onto vibratable mesh for aerosolization. Restrictor defines a plurality of apertures that provide increases in pressure differential that vary with inspiratory flow rate within conduit and provide relatively laminar flow downstream of
(Continued)

restrictor. Indicator mechanism indicates a state of flow parameters relative to a predefined range. Aerosol generator is configured to aerosolize at least a portion of liquid medicament only when flow parameters of the inspiratory flow are within range.

18 Claims, 11 Drawing Sheets

(52) U.S. Cl.
CPC ... *A61M 15/0085* (2013.01); *A61M 2016/003* (2013.01); *A61M 2016/0021* (2013.01); *A61M 2016/0027* (2013.01); *A61M 2205/3331* (2013.01); *A61M 2205/502* (2013.01); *A61M 2205/52* (2013.01); *A61M 2205/581* (2013.01); *A61M 2205/582* (2013.01); *A61M 2205/584* (2013.01); *A61M 2205/6018* (2013.01); *A61M 2205/6054* (2013.01); *A61M 2205/6072* (2013.01); *A61M 2205/8206* (2013.01); *A61M 2206/11* (2013.01)

(58) Field of Classification Search
CPC .... A61M 2016/0027; A61M 2016/003; A61M 2205/3331; A61M 2205/502; A61M 2205/52; A61M 2205/581; A61M 2205/582; A61M 2205/584; A61M 2205/6018; A61M 2205/6054; A61M 2205/8206; A61M 2206/11
See application file for complete search history.

(56) References Cited

U.S. PATENT DOCUMENTS

| | | | |
|---|---|---|---|
| 5,060,642 A | 10/1991 | Gilman | |
| 5,164,740 A | 11/1992 | Ivri | |
| 5,320,094 A | 6/1994 | Laube et al. | |
| 5,333,106 A | 7/1994 | Lanpher et al. | |
| 5,347,998 A | 9/1994 | Hodson et al. | |
| 5,363,842 A | 11/1994 | Mishelevich et al. | |
| 5,364,838 A * | 11/1994 | Rubsamen | A61K 9/007 514/5.9 |
| 5,479,920 A | 1/1996 | Piper et al. | |
| 5,515,842 A | 5/1996 | Ramseyer et al. | |
| 5,544,646 A * | 8/1996 | Lloyd | A61K 51/1206 128/200.14 |
| 5,586,550 A | 12/1996 | Ivri et al. | |
| 5,655,520 A | 8/1997 | Howe et al. | |
| 5,672,581 A | 9/1997 | Rubsamen et al. | |
| 5,743,250 A * | 4/1998 | Gonda | A61K 9/007 128/200.14 |
| 5,758,637 A * | 6/1998 | Ivri | A61M 11/005 128/200.14 |
| 5,884,620 A | 3/1999 | Gonda et al. | |
| 5,915,378 A | 6/1999 | Lloyd et al. | |
| 5,938,117 A | 8/1999 | Ivri | |
| 5,941,240 A | 8/1999 | Gonda et al. | |
| 6,014,970 A * | 1/2000 | Ivri | A61M 15/0085 128/200.14 |
| 6,085,740 A | 7/2000 | Ivri et al. | |
| 6,085,753 A | 7/2000 | Gonda et al. | |
| 6,098,615 A | 8/2000 | Lloyd et al. | |
| 6,109,261 A | 8/2000 | Clarke et al. | |
| 6,131,567 A | 10/2000 | Gonda et al. | |
| 6,205,999 B1 | 3/2001 | Ivri et al. | |
| 6,312,665 B1 | 11/2001 | Modi | |
| 6,408,854 B1 | 6/2002 | Gonda et al. | |
| 6,427,682 B1 | 8/2002 | Klimowicz et al. | |
| 6,467,476 B1 | 10/2002 | Ivri et al. | |
| 6,534,701 B2 | 3/2003 | Isozaki | |
| 6,540,153 B2 | 4/2003 | Ivri | |
| 6,540,154 B1 | 4/2003 | Ivri et al. | |
| 6,629,646 B1 | 10/2003 | Ivri | |
| 6,640,804 B2 | 11/2003 | Ivri et al. | |
| 6,647,987 B2 | 11/2003 | Gonda et al. | |
| 6,655,379 B2 * | 12/2003 | Clark | A61K 9/0073 128/203.12 |
| 6,681,762 B1 | 1/2004 | Scheuch et al. | |
| 6,688,304 B2 | 2/2004 | Gonda et al. | |
| 6,755,189 B2 | 6/2004 | Ivri et al. | |
| 6,814,071 B2 | 11/2004 | Klimowicz et al. | |
| 6,921,020 B2 | 7/2005 | Ivri | |
| 6,926,208 B2 | 8/2005 | Ivri | |
| 6,978,941 B2 | 12/2005 | Litherland et al. | |
| 7,028,686 B2 | 4/2006 | Gonda et al. | |
| 7,032,590 B2 | 4/2006 | Loeffler et al. | |
| 7,040,549 B2 | 5/2006 | Ivri et al. | |
| 7,066,398 B2 | 6/2006 | Borland et al. | |
| 7,083,112 B2 | 8/2006 | Ivri | |
| 7,100,600 B2 | 9/2006 | Loeffler et al. | |
| 7,108,197 B2 | 9/2006 | Ivri | |
| 7,131,440 B2 | 11/2006 | Sonntag | |
| 7,174,888 B2 | 2/2007 | Ivri et al. | |
| 7,185,651 B2 | 3/2007 | Alston et al. | |
| 7,195,011 B2 | 3/2007 | Loeffler et al. | |
| 7,219,664 B2 | 5/2007 | Ruckdeschel et al. | |
| 7,364,571 B2 | 4/2008 | Schinazi et al. | |
| 7,448,375 B2 | 11/2008 | Gonda et al. | |
| 7,451,760 B2 | 11/2008 | Denyer et al. | |
| 7,600,512 B2 | 10/2009 | Lee et al. | |
| 7,628,339 B2 | 12/2009 | Ivri et al. | |
| 7,683,029 B2 | 3/2010 | Hindle et al. | |
| 7,748,382 B2 | 7/2010 | Denyer et al. | |
| 7,819,115 B2 | 10/2010 | Sexton et al. | |
| 7,891,358 B2 | 2/2011 | Kolb et al. | |
| 7,913,688 B2 | 3/2011 | Cross et al. | |
| 8,082,918 B2 | 12/2011 | Jansen et al. | |
| 8,950,394 B2 | 2/2015 | Patton et al. | |
| 9,004,061 B2 | 4/2015 | Patton et al. | |
| 2001/0037805 A1 | 11/2001 | Gonda et al. | |
| 2001/0039948 A1 | 11/2001 | Sexton et al. | |
| 2003/0019493 A1 | 1/2003 | Narayan et al. | |
| 2003/0047620 A1 | 3/2003 | Litherland et al. | |
| 2004/0134494 A1 | 7/2004 | Papania et al. | |
| 2005/0011514 A1 * | 1/2005 | Power | A61M 15/0085 128/200.14 |
| 2006/0239930 A1 | 10/2006 | Lamche et al. | |
| 2007/0113841 A1 | 5/2007 | Fuchs | |
| 2007/0163572 A1 | 7/2007 | Addington et al. | |
| 2008/0029083 A1 | 2/2008 | Masada et al. | |
| 2008/0060641 A1 | 3/2008 | Smith et al. | |
| 2008/0233053 A1 | 9/2008 | Gross et al. | |
| 2009/0056708 A1 | 3/2009 | Stenzler et al. | |
| 2009/0157037 A1 | 6/2009 | Iyer et al. | |
| 2009/0301472 A1 | 12/2009 | Kim et al. | |
| 2010/0075001 A1 | 3/2010 | Succar et al. | |
| 2010/0078015 A1 | 4/2010 | Imran | |
| 2010/0089395 A1 * | 4/2010 | Power | A61M 11/003 128/203.15 |
| 2010/0204602 A1 * | 8/2010 | Addington | A61M 11/02 600/538 |
| 2010/0319686 A1 | 12/2010 | Schennum | |
| 2011/0114089 A1 | 5/2011 | Andersen et al. | |
| 2011/0168170 A1 | 7/2011 | Patton et al. | |
| 2011/0168172 A1 | 7/2011 | Patton et al. | |
| 2011/0226242 A1 | 9/2011 | Von Hollen et al. | |
| 2012/0048268 A1 | 3/2012 | Hyun et al. | |
| 2012/0291776 A1 * | 11/2012 | Van Der Mark | A61M 11/005 128/200.14 |
| 2013/0269684 A1 | 10/2013 | Patton | |
| 2013/0269694 A1 | 10/2013 | Patton et al. | |
| 2014/0041653 A1 | 2/2014 | Patton et al. | |
| 2014/0116426 A1 * | 5/2014 | Mullinger | A61M 15/0071 128/200.14 |

FOREIGN PATENT DOCUMENTS

| | | |
|---|---|---|
| RU | 2033816 C1 | 4/1995 |
| RU | 2232023 C2 | 7/2004 |
| RU | 2427392 C2 | 8/2011 |

(56) References Cited

FOREIGN PATENT DOCUMENTS

| WO | 91/11050 | 7/1992 |
| WO | 1998/22290 | 5/1998 |
| WO | 2003/030829 | 4/2003 |
| WO | 2004/028608 | 4/2004 |
| WO | 2006/062449 | 6/2006 |
| WO | 2007/047948 | 4/2007 |
| WO | 2008/058941 A1 | 5/2008 |

OTHER PUBLICATIONS

International Patent Application No. PCT/US2015/037505, "International Search Report and Written Opinion" dated Sep. 29, 2015, 10 pages.
International Patent Application No. PCT/US2015/037505, "International Preliminary Report on Patentability" dated Jan. 12, 2017, 8 pages.
EP 15814884.1 received an Extended European Search Report, dated Jun. 14, 2018, 9 pages.
RU2017103012 received an Office Action dated Dec. 5, 2018, 10 pages.
CN Application No. CN201580046705.X received an Office Action dated Aug. 20, 2018, 6 pages.
Brazil Application No. BR112016030883-2 received an Office Action dated May 5, 2020, 7 pages.

* cited by examiner

LIQUID NEBULIZATION SYSTEMS AND METHODS

CROSS REFERENCE TO RELATED APPLICATIONS

This application claims the benefit of U.S. Provisional Application No. 62/019,781, filed on Jul. 1, 2014, entitled "LIQUID NEBULIZATION SYSTEMS AND METHODS," the entire disclosure of which is hereby incorporated by reference, for all purposes, as if fully set forth herein.

BACKGROUND OF THE INVENTION

Aerosolization systems provide effective delivery for a variety of medicaments, such as insulin and asthma medications. Such systems deliver the medicaments directly to a user's respiratory system by aerosolizing a metered dose of the medicament in liquid form. The user then inhales the aerosolized medicament directly into the respiratory system, enabling faster treatment of various medical conditions.

Delivery of consistent and properly metered doses of aerosolized medicament to a user is very important. Current aerosolization systems often provide inconsistent doses by having some of the medicament remain in a reservoir in liquid form after the aerosolization process. Additionally, the aerosolized medicament is often delivered with too great or too little force for substantially all of the metered dose to properly enter the user's respiratory system. A further problem of current aerosolization systems is a tendency for the medicament to become contaminated by the user or other sources. Contamination of the medicament is particularly problematic since some or all of the contaminated medicament is thereafter delivered directly to the user's respiratory system. Embodiments of the invention may provide solutions to these and other problems.

BRIEF SUMMARY OF THE INVENTION

In one embodiment, an aerosolization device for delivering aerosolized medicament to a user is provided. The aerosolization device may include a conduit, an aerosol generator in communication with the conduit, a fluid receiving chamber in communication with the aerosol generator, a restrictor disposed within the conduit, and an indicator mechanism. The conduit may have an inner wall and a mouthpiece end by which a user may cause an inspiratory flow through the conduit. The aerosol generator may include a vibratable mesh where the vibratable mesh may be laterally offset from the inner wall. The fluid receiving chamber may receive a volume of a liquid medicament. At least a portion of the fluid receiving chamber may be tapered such that substantially all of the liquid medicament may be directed onto the vibratable mesh for aerosolization. The restrictor may define a plurality of apertures. The plurality of apertures may be configured to provide an increase in pressure differential that varies with an inspiratory flow rate within the conduit and to provide a relatively laminar flow downstream of the restrictor compared to upstream of the restrictor plate. The indicator mechanism may indicate to a user a state of one or more flow parameters relative to a predefined desired range. The aerosol generator may be configured to aerosolize at least a portion of the volume of the liquid medicament only when the one or more flow parameters of the inspiratory flow are within the desired range.

In another embodiment, a different aerosolization device for delivering aerosolized medicament to a user is provided. The aerosolization device may include a conduit, an aerosol generator in communication with the conduit, and a fluid receiving chamber in communication with the aerosol generator. The conduit may be attachable to a housing. The conduit may have an inner wall and a mouthpiece end by which a user may cause an inspiratory flow through the conduit. The aerosol generator may include a vibratable mesh. The vibratable mesh may be laterally offset from the inner wall by about 1 millimeter (mm) and 6 mm. The aerosol generator may receive a volume of a liquid medicament and at least a portion of the fluid receiving chamber may be tapered such that substantially all of the liquid medicament may be directed onto the vibratable mesh for aerosolization. The aerosol generator may be configured to aerosolize at least a portion of the volume of liquid medicament only when one or more flow parameters of an inspiratory flow are within a predefined desired range.

In another embodiment, a method of delivering an aerosolized medicament to a user's respiratory system is provided. The method may include sensing a state of a flow parameter of an inspiratory flow within a conduit. The conduit may have an inner wall and a mouthpiece end by which a user may cause the inspiratory flow within the conduit. The method may also include vibrating a mesh of an aerosol generator in communication with the conduit to aerosolize a volume of a liquid medicament to produce a plume of aerosolized medicament within the conduit when the state of the flow parameter is within a predefined desired range. The mesh may be laterally offset from the inner wall. The plume of aerosolized medicament may be carried toward the mouthpiece end of the conduit.

BRIEF DESCRIPTION OF THE DRAWINGS

The present invention is described in conjunction with the appended figures.

Figure 1A:
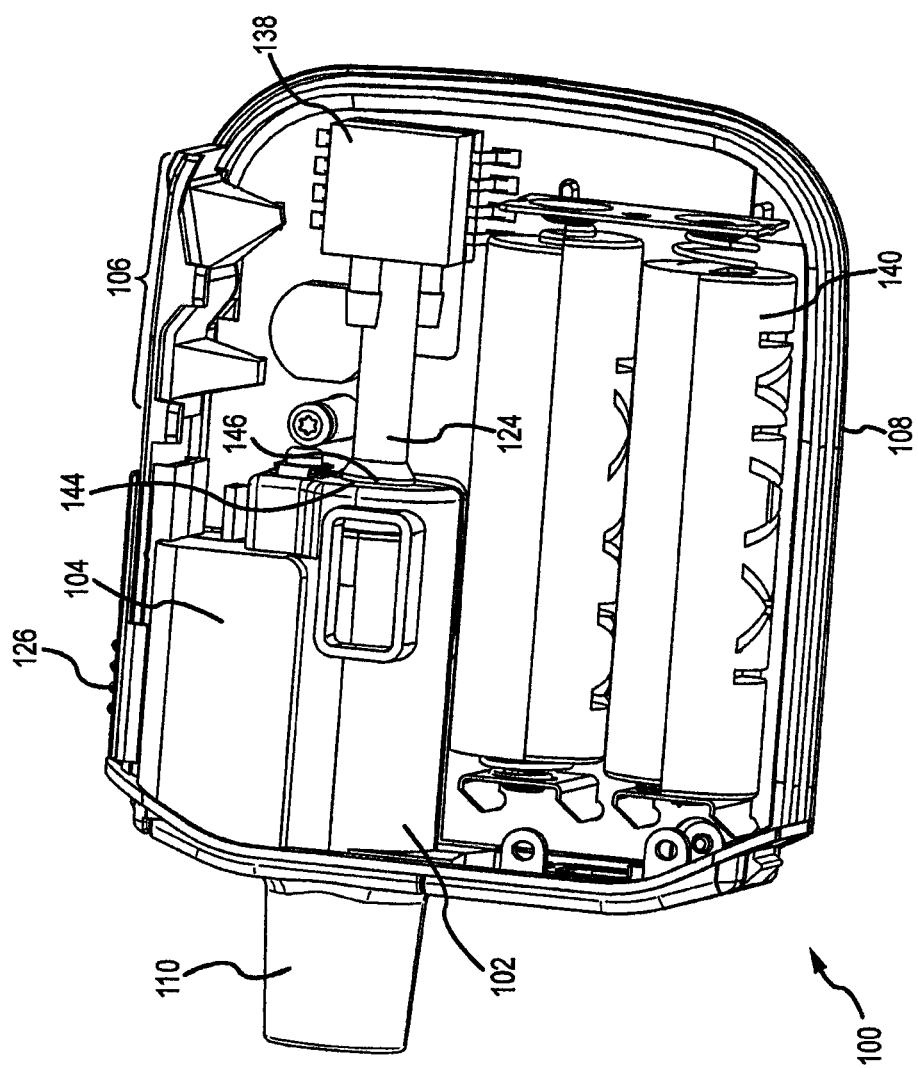
FIG. 1A depicts an interior of an aerosolization device according to embodiments of the invention.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The ensuing description provides exemplary embodiments only, and is not intended to limit the scope, applicability or configuration of the invention. Rather, the ensuing description of exemplary embodiments will provide those skilled in the art with an enabling description for implementing various embodiments of the invention. It will be understood that various changes may be made in the function and arrangement of elements without departing from the spirit and scope of the invention as set forth in the appended claims. For example, any detail discussed with regard to one embodiment may or may not be present in variations of that embodiment, and/or in other embodiments discussed herein.

Embodiments of an aerosolization device for assisting in proper delivery of an uncontaminated dose of aerosolized medication to a user's respiratory system are described herein. In many embodiments, liquid medicament may be provided to an aerosolization device in a metered dose. The liquid medicament may be dispensed to an aerosol generator. In some embodiments, the liquid medicament may be provided via a chamber or reservoir that funnels the liquid medicament into the aerosol generator where the liquid medicament is aerosolized for delivery into a user's respiratory system. In some embodiments, a separate container holding the liquid medicament may couple with the aerosolization device to provide the liquid medicament thereto. The aerosol generator may be configured to aerosolize at least a portion of the volume of the liquid medicament only when the one or more flow parameters of the inspiratory flow are within a desired range.

In some embodiments, the aerosolization device may include a conduit, an aerosol generator in communication with the conduit, a fluid receiving chamber in communication with the aerosol generator, a restrictor plate disposed within the conduit, and an indicator mechanism. In many embodiments, some or all of these components are disposed within a housing. In some embodiments, the conduit and/or the aerosol generator may be removably coupled with or received within the housing. By providing a removable conduit and/or aerosol generator, the aerosolization device may be easily cleaned, thus preventing contamination and buildup of pathogens and/or other contaminants. The removal of the components also helps in drying the components. As the aerosolization device is quickly and easily cleaned and dried in this manner, no standing liquid remains that could lead waterborne bacteria to proliferate.

In some embodiments, the conduit may include an inner wall and a mouthpiece end by which a user may cause an inspiratory flow through the conduit. A user may inhale through the mouthpiece to create the inspiratory flow of air that may transport an aerosolized medicament to the user. In some embodiments, the mouthpiece end of the conduit may deliver the aerosolized medicament to the user at an angle relative to a horizontal plane. Such a delivery angle may be selected based on the dosage and type of medicament to be delivered to the user's respiratory to ensure that a substantial portion of the aerosolized medicament is delivered to the respiratory system without becoming stuck in the user's mouth, throat, and/or other area.

In many embodiments, a sensor is used to determine when a parameter of the inspiratory flow is within a predefined desired or operating range of the aerosolization device and/or the aerosol generator. For example, a flow sensor or pressure transducer may be used to determine a flow rate or pressure differential within the conduit. Other types of sensors and flow parameters may also be employed/measured. For example, the flow parameter can be an inspiratory flow rate, inspiratory pressure, inspiration time, and the like detected by a flow sensor, timer, pressure transducer, or other sensing mechanism. A processing unit coupled with the sensor may compare the sensed value to a stored desired range. In some embodiments, the desired range of a flow parameter for a particular medicament delivery may correspond to the operating range of the aerosol generator. In other embodiments, the desired range of a flow parameter may be narrower or broader than the operating range of the aerosol generator.

In some embodiments, the aerosol generator may include a vibratable mesh that is in fluid communication with the conduit. The vibratable mesh may be domed shaped and be vibrated by an annular piezoelectric element (not shown) or other electro-mechanical resonating device that circumscribes the vibratable mesh. The vibratable mesh is vibrated when one or more flow parameters are within an operating range of the aerosol generator. For example, a flow sensor and/or pressure transducer in communication with the conduit may detect that an inspiratory flow rate and/or a pressure differential within the conduit is within an operating range of the aerosol generator. A processor may control a circuit to provide an electric current to the piezoelectric element to vibrate the mesh. Typically, the vibratable mesh will be vibrated at a frequency in the range from about 50 kHz to about 150 kHz to aerosolize the dose of liquid medicament.

The vibratable mesh may be disposed at a distance from the inner wall of the conduit such that a lower surface of the vibratable mesh is offset from the most proximate wall of the conduit. This offset ensures that substantially all of any pathogens or other contaminants that are introduced to the conduit will be deposited onto surfaces other than the vibratable mesh, thereby maintaining a clean and/or sterile source of aerosolized medicament. Such pathogens and/or contaminants may be introduced to the aerosolization system by the user via a cough, sneeze, or other action or by an environmental source.

In some embodiments, the vibratable mesh may define a plurality of apertures. The plurality of apertures may include more than 500 apertures. In some embodiments, the plurality of apertures may include more than 1000 apertures. Each aperture may have an exit diameter ranging from about 1 µm to about 8 µm, preferably from about 3 µm to about 6 µm, and in some cases around 4 µm. Due to the combination of small aperture size and being offset from the conduit, the vibratable mesh and reservoir can stay substantially clean to produce an uncontaminated plume of aerosolized medicament.

In some embodiments, the fluid receiving chamber may receive a volume of a liquid medicament to be aerosolized. Any medicament that is not deposited directly onto the vibratable mesh can be funneled or otherwise directed onto the vibratable mesh by tapered walls of the fluid receiving chamber such that substantially all of the liquid medicament may be directed onto the vibratable mesh for aerosolization. The fluid receiving chamber can be configured to have not more than 15 μl of the liquid medicament remain within the fluid receiving chamber after aerosolization. By dispensing the entire dose or substantially all of the dose, the vibratable mesh is kept essentially free of liquid from one dose to the next. Any remaining liquid will air dry between doses. In some instances, the time between doses may be between about 45 minutes and 2 hours. In this way, it is thereby possible to avoid contact between liquid and ambient air during periods of non-use between successive uses. For pharmaceutical preparations this is particularly important since it may obviate the need for the use of preservatives in the liquid and avoids evaporative losses. For example, various preservative free insulin formulations that may be used include those described in U.S. application Ser. No. 13/004,662, entitled "Preservative Free Insulin Formulations and Systems and Methods for Aerosolizing," which is hereby incorporated by reference in its entirety.

In many embodiments, the inhaled air may pass through a restrictor array within the conduit. In some embodiments, the restrictor array may be a restrictor plate that has a plurality of apertures passing therethrough. As air passes through the apertures, the apertures provide an increase in pressure differential that varies according to the inspiratory flow rate within the conduit. The apertures also provide a relatively laminar flow downstream of the restrictor plate compared to upstream of the restrictor plate. In many embodiments, the apertures are disposed along an outer periphery of the restrictor plate. In some embodiments, the vibratable mesh may be located downstream of the restrictor plate or other restrictor array and produce a plume of aerosolized medicament within the relatively laminar flow produced by the restrictor array. In some embodiments, the restrictor array may include multiple restrictor plates in series.

The indicator mechanism may indicate to a user a state of a parameter of the inspiratory flow relative to a predefined desired range. For example, the indicator may be a light, analog/digital display or readout, speaker, vibration-generating device, and/or other feature that alerts a user as to the state of the parameter. In some embodiments, the state of the parameter can be an inspiratory flow rate, inspiratory pressure, inspiration time, and the like detected by a flow sensor, timer, pressure transducer, or other sensing mechanism. The indicator may inform the user if they are within or outside of the desired range for the parameter.

In some embodiments, an 'end of dose' indication can be provided to a user when an entire dose of the medicament has been aerosolized. Such an indication may be provided upon a sensor, such as a load or flow sensor, detects that substantially all of the medicament has been aerosolized. Another indication may also be provided to the user informing them of when the liquid medicament is actually being aerosolized by the activated vibratable mesh. Such indications can be provided by the indicator mechanism described above, such as by providing a distinguishable indication from the indication of the state of the flow parameter. For example, the state of the flow parameter may be indicated by a green light and the indication of the end of dose may be provided by a blue light. In other embodiments, the end of dose indication and/or the aerosolization indication may be provided by one or more separate indicator mechanisms.

In some embodiments, the aerosolization device may further include an input device for receiving and setting the predefined desired range of the parameter of the inspiratory flow. For example, the input device may include a barcode scanner, radio frequency identification (RFID) reader, keyboard, or any other input device that can receive an input from the user regarding one or more parameters of the inspiratory flow, such as a desired flow rate, inspiratory pressure, or inspiration time. In some embodiments, the desired flow rate may be visually or otherwise encoded on the medicament delivery container, and read by the aerosolization device therefrom.

In some embodiments, the parameter of the inspiratory flow may include the inspiratory flow rate within the conduit. The predefined desired range of the inspiratory flow rate may be between about 5 and 14 liters per minute (L/min). In some embodiments, the parameter of the inspiratory flow may include the inspiration time. The predefined desired range of the inspiration time may be between about 5 and 26 seconds. In some embodiments, multiple parameters may be measured and referred to. For example, in one embodiment, a certain amount of inspiration time of a minimum inspiratory flow may be necessary.

In some embodiments, the aerosolization system may include electronic elements including, but not limited to, a processing element and a memory unit. The processing element may be used to control the actuation of the aerosol generator, indicator mechanisms, and input devices, as well as any sensors such as flow sensors and pressure transducers. The memory unit may be configured to store settings and ranges set by the input device for the parameters of the indicator mechanism and/or aerosol generator. The memory unit may also be configured to store data related to past aerosolization sessions, as well as information provided by medicament delivery vessels attached thereto.

Figure 1B:
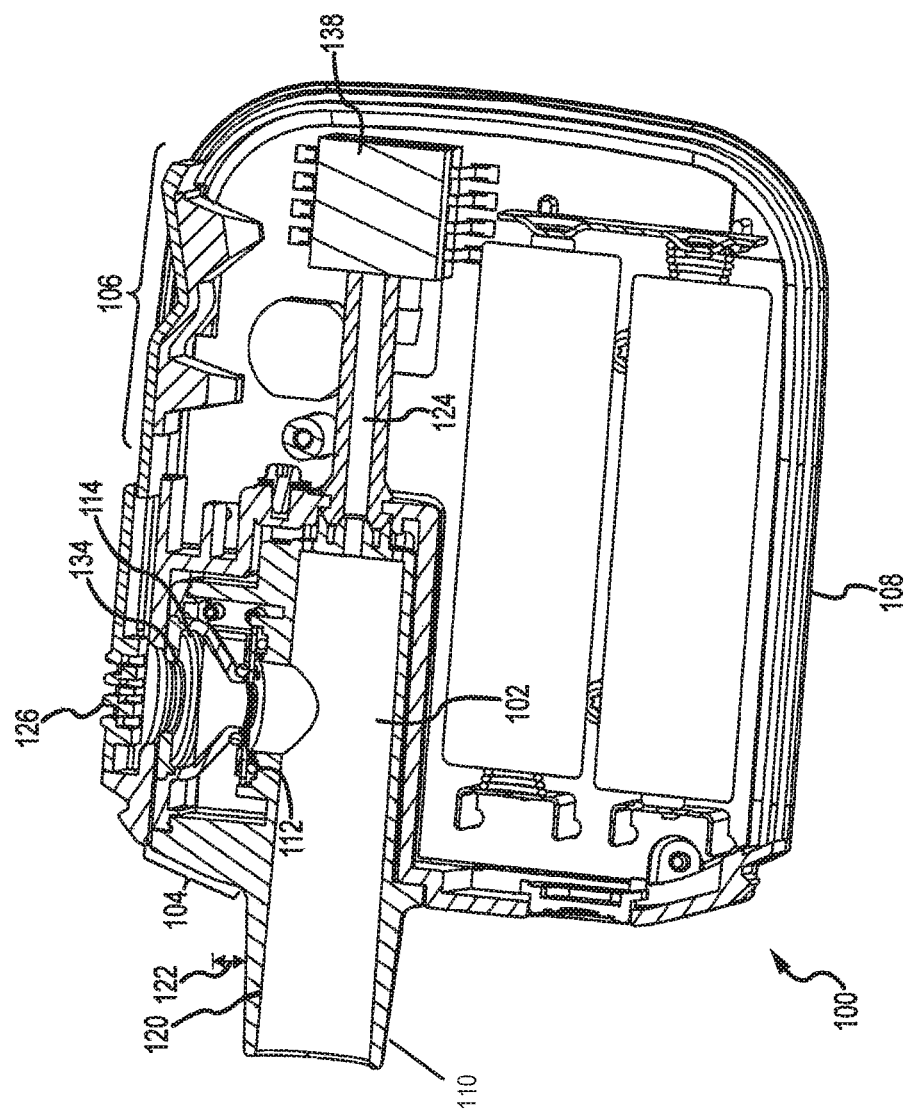
FIG. 1B shows a cross section of FIG. 1A according to embodiments of the invention.

Turning now to the drawings, FIGS. 1A and 1B illustrate an aerosolization device 100, in accordance with various embodiments of the invention. Aerosolization device 100 includes a conduit 102 and an aerosol generator 104 in communication with the conduit 102. The aerosolization device 100 may also include one or more indicator mechanisms 106, shown here as indicator lights. The one or more indicator mechanisms may be coupled with a housing 108 or some other portion of device 100. Conduit 102 and aerosol generator 104 may also optionally be coupled with housing 108.

In some embodiments, conduit 102 may include a mouthpiece end 110 through which a user may inhale to produce an inspiratory flow to deliver aerosolized medicament to the user's respiratory system. As seen in FIG. 1B, the conduit 102 defines an inner wall 120. The aerosol generator 104 may include a vibratable mesh 112. Liquid medicament can be dispensed onto the vibratable mesh 112, either directly from a vial of liquid medicament or indirectly by being funneled onto the vibratable mesh 112 by tapered walls of a fluid receiving chamber 114. In many embodiments, the vibratable mesh 112 is vibrated via a mechanism controlled by a processor to aerosolize a volume of liquid medicament when a flow rate of the inspiratory flow is within an operating range of the aerosol generator 104. When vibrated, the vibratable mesh 112 operates to produce a plume of aerosolized medicament within the conduit 102 such that the aerosolized conduit can be inhaled into the user's lungs.

Exemplary aerosol generators that can be used are also described in U.S. Pat. Nos. 5,164,740; 6,629,646; 6,926,208; 7,108,197; 5,938,117; 6,540,153; 6,540,154; 7,040,549; 6,921,020; 7,083,112; 7,628,339; 5,586,550; 5,758,637; 6,085,740; 6,467,476; 6,640,804; 7,174,888; 6,014,970; 6,205,999; 6,755,189; 6,427,682; 6,814,071; 7,066,398; 6,978,941; 7,100,600; 7,032,590; 7,195,011, incorporated herein by reference. These references describe exemplary aerosol generators, ways to manufacture such aerosol generators and ways to supply liquid to aerosol generators, and are incorporated by reference for at least these features.

In some embodiments, the vibratable mesh may be disposed at a distance 122 from the inner wall 120 of the conduit 102. For example, vibratable mesh 112 may be disposed at a distance 122 between about 1 mm and 6 mm from the inner wall 120. The vibratable mesh 112 may define a plurality of apertures from which the aerosolized medicament is dispersed into the conduit 102. In some embodiments, the plurality of apertures may include more than 500 apertures, each aperture having a diameter between about 1 and 8 μm. In other embodiments, the plurality of apertures may include more than 1000 apertures. The small size of the apertures in conjunction with the vibratable mesh 112 being offset from the conduit 102 helps ensure that the aerosolized medicament is uncontaminated. The vibratable mesh 112 may be dome shaped and be vibrated by an annular piezoelectric element (not shown) that circumscribes the apertures. The diameter of the vibratable mesh 112 may be in the range from about 5 mm to about 8 mm. The vibratable mesh 112 may also have a thickness in the range from about 50 microns to about 70 microns. Typically, the vibratable mesh 112 will be vibrated at a frequency in the range from about 50 kHz to about 150 kHz to aerosolize the dose of liquid medicament.

In some embodiments, the conduit 102 may include an opening 134 that provides access to the fluid receiving chamber 114. The opening 134 may have a diameter that is smaller than a diameter 136 of a top of the fluid receiving chamber 114. Such geometry ensures that sides of a tip of a dispenser of liquid medicament cannot contact the walls of the fluid receiving chamber 114, and also provides a contact point for a shoulder of a dispensing mechanism to prevent the dispenser tip from contacting the vibratable mesh 112. By preventing such contact, the tip cannot contact a volume of liquid medicament within the fluid receiving chamber 114 and pull some of the volume out of the fluid receiving chamber 114 and/or contaminate the liquid medicament.

In some embodiments, the aerosolization device 100 include a processing unit or integrated circuit (IC) 138 that controls the function of or runs computer code to control other electronic components of the aerosolization device 100. Aerosolization device 100, including IC 138, may be powered by batteries 140 that are coupled with IC 138. IC 138 may be electrically coupled with electronic components, such as any sensors, indicating mechanisms 106 and/or a piezoelectric element of aerosol generator 104. IC 138 can control the actuation of the indicator mechanisms and/or the aerosol generator 104 based on information received from any sensors, such as flow sensors or pressure transducers in fluid communication with the conduit 102. In some embodiments, IC 138 may be electrically coupled with the conduit 102 and/or the aerosol generator 104 using a plug 124. The conduit 102 and/or aerosol generator 104 may be removable from housing 108. The conduit 102 and/or aerosol generator 104 may be inserted into housing 108 and interfaced with plug 124 to supply power to and control actuation of the aerosol generator 104 based on measurements from sensors in fluid communication with conduit 102.

Figure 2:
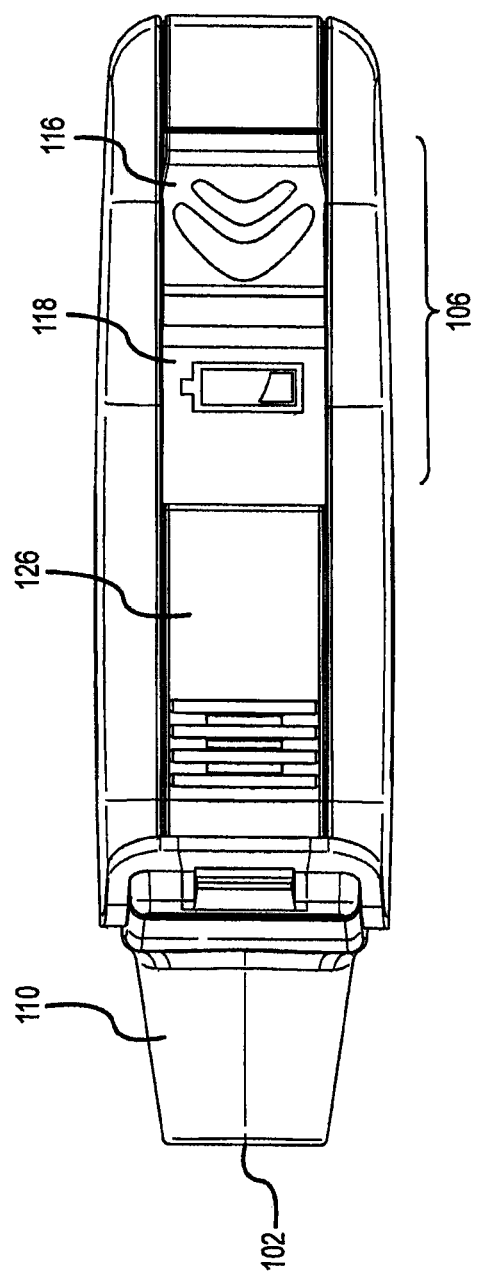
FIG. 2 depicts a front of the aerosolization device of FIG. 1A according to embodiments of the invention.

FIG. 2 shows a top view of aerosolization device 100 and indicator mechanisms 106 according to embodiments of the invention. In some embodiments, indicator mechanisms 106 can include a breathing indicator 116 and a battery indicator 118. Breathing indicator 116 can direct a user when and how to breath to maximize delivery of the aerosolized medicament to the user's lungs. In some embodiments, breathing indicator 116 can include multiple indicators, such as various colored LEDs, to provide the user more detailed guidance. Breathing indicator 116 may be in the shape of a chevron that includes 3 colors of LEDs.

In some embodiments, optimal pulmonary delivery of medicaments such as liquid insulin occurs at specified flow rates and inspiratory times. For example, an optimal flow rate may be between about 5 and 14 L/min, or more often between about 7 and 14 L/min. Flow rates that are too high or too low can result in losses in the amount of aerosolized medicament delivered to the proper locations of a user's respiratory system. An optimal inspiratory time may be between 6 and 24 seconds. Breathing indicator 116 can be used to direct a user to maintain an inhalation within these parameters.

The breathing indicator 116 may produce a different colored light as an "end of dose" indictor to indicate that substantially all of the dose of medicament has been delivered. For example, a blue light may be emitted for a period of time, such as between about 1 and 10 seconds to alert the user that substantially all of the dose has been aerosolized and inhaled. Delivery of the entire dose may be predefined as when at least about 95% of the dose is delivered, more preferably 98% and most preferably when more than 99% of the dose is aerosolized. To receive the dose, the user may take several inhalations or a single inhalation depending on the volume of liquid drug to be delivered and the user's breathing capacity. Each inhalation may be monitored by the device, with feedback provided to the user via indicator 116, to insure proper delivery to the lungs. In some embodiments, the operation of the end of dose indicator may be delayed for a period, such as up to about 5 seconds after substantially all of the dose has been delivered, thus providing a "chaser" of air into the lungs. This chaser may serve to clear the upper airway and maximize the amount of the dose that is transported to the user's lungs.

In some embodiments, a cover 126 may be coupled with the fluid receiving chamber 114 and/or housing 108 to seal the fluid receiving chamber 114 and the vibratable mesh 112 when in a closed position. The cover 126 operates to prevent pathogens or other contaminants from entering the fluid receiving chamber 114. The cover 126 may operate to expose the fluid receiving chamber 114 and vibratable mesh 112 when in an open position. Cover 126 may include a sliding mechanism (not shown) such that the cover 126 may be moved from an open position to a closed position and back by sliding the cover 126 within or on a track. In some embodiments, the cover 126 is hinged such that the cover 126 may be flipped open and closed. A latching mechanism (not shown) may be included to maintain cover 126 in a closed position.

Figure 3:
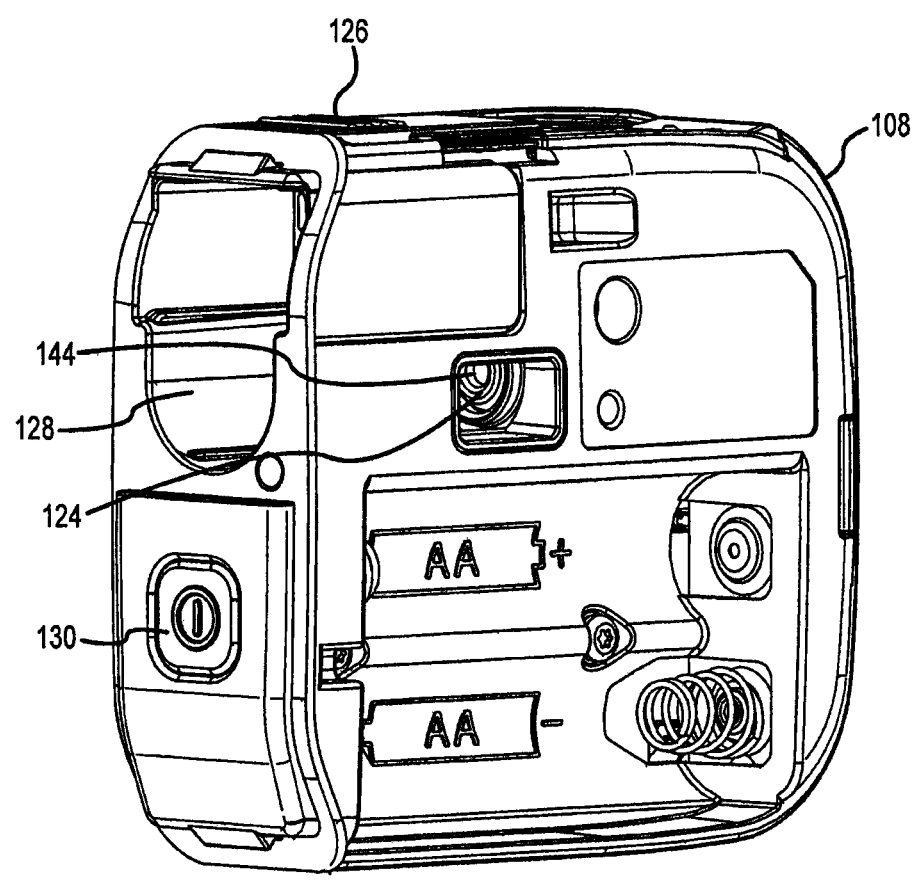
FIG. 3 illustrates a housing of the aerosolization device of FIG. 1A with the conduit and aerosol generator removed according to embodiments of the invention.

In some embodiments, one or both of conduit 102 and aerosol generator 104 are removably coupled with housing 108. FIG. 3 shows an isometric view of aerosolization device 100 having conduit 102 and aerosol generator 104 removed from an opening 128 within housing 108. Opening 128 may be configured to slidingly receive and secure one or both of conduit 102 and aerosol generator 104. Power button 130 may be included to activate the aerosolization device 100. Plug 124 may be positioned within opening 128 to couple the conduit 102 and/or aerosol generator 104 with the IC 138. Male connector 144 of plug 124 can interface with female connector 146 of conduit 102.

Figure 4A:
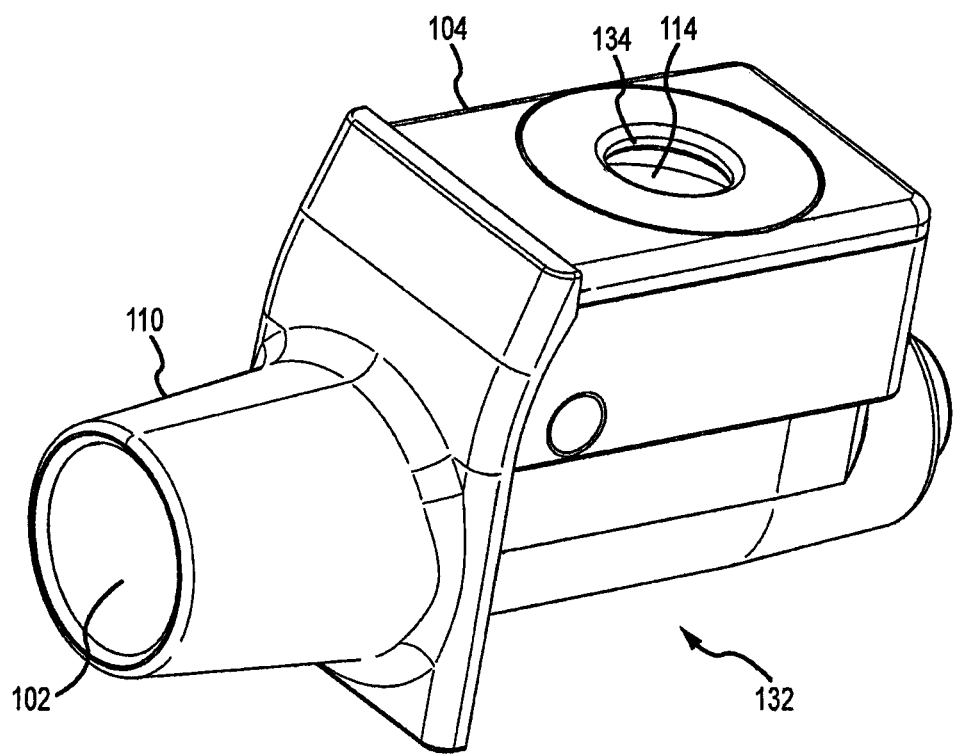
FIGS. 4A and 4B depict the conduit and aerosol generator of the aerosolization device of FIG. 1 removed from the housing according to embodiments of the invention.
Figure 4B:
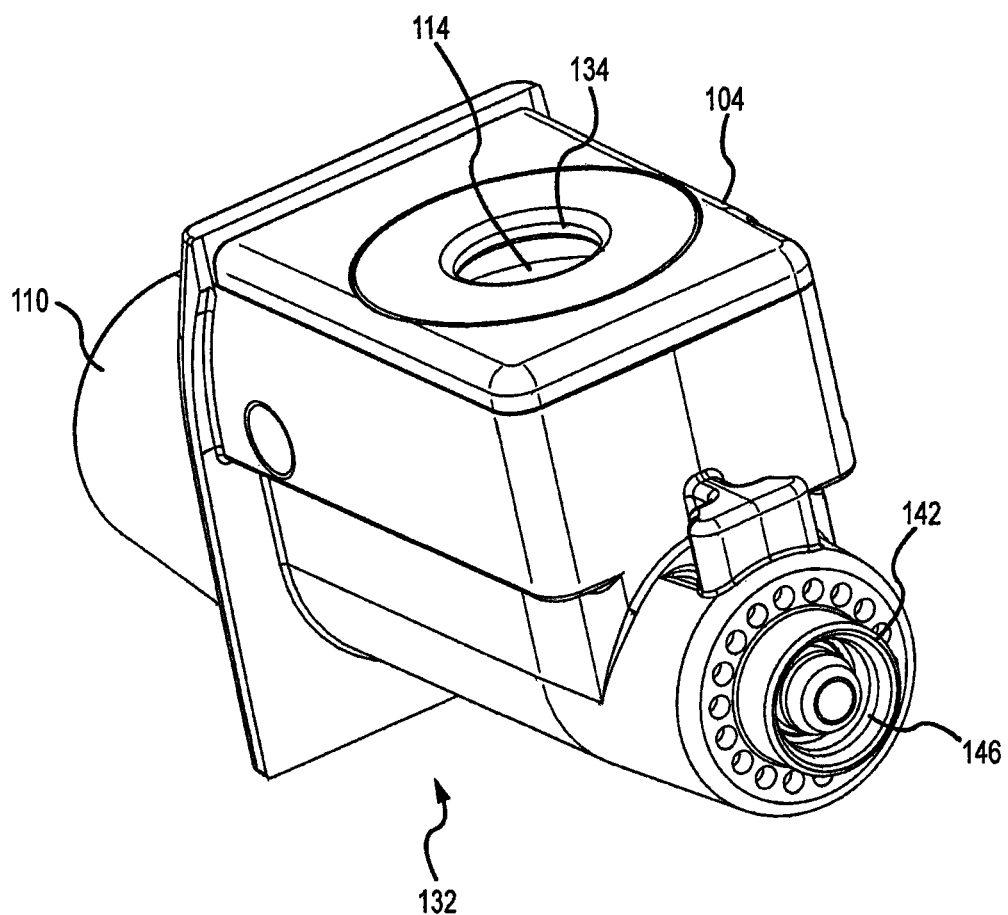

FIGS. 4A and 4B show conduit 102 and aerosol generator 104 removed from housing 108. Conduit 102 and aerosol generator 104 may be separate components and/or share and exterior housing 132. The exterior housing 132 may be configured to slide into opening 128 of housing 108. In some embodiments, the exterior housing 132 may include an electrical connector 142, as shown in FIG. 4B. Electrical connection 142 may couple with plug 124 as seen in FIGS. 1A, 1B, and 3 to couple the conduit 102 and/or aerosol generator 104 to IC 138. Electrical connection 142 can include a female or male connection and couple with a corresponding connection on the plug 124. For example, female connector 146 may interface with male connector 144 of plug 124. In this manner, the exterior housing 132, aerosol generator 104, and/or conduit 102 may be removed for replacement while the housing 108, IC 138, and other components may be reused. The electric and/or control components are often more expensive to replace than the exterior housing 132, aerosol generator 104, and/or conduit 102, so such reuse provides a cost effective solution when some components need to be replaced.

Figure 5:
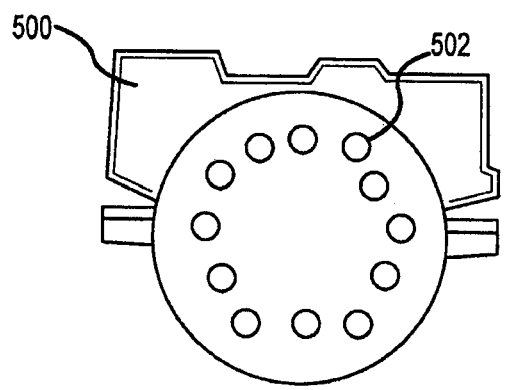
FIG. 5 illustrates restrictor plates according to embodiments of the invention.

FIG. 5 depicts an embodiment of a flow restrictor plate that may be positioned within a conduit, such as conduit 102 of FIGS. 1, 1A, 2, and 4. Restrictor plate 10 creates resistance to and limits airflow through a conduit while adding minimal to no length to a conduit. The restrictor plate 500 provides an increase in pressure differential that varies with inspiratory flow rates. This pressure differential exists between the conduit and outside of the conduit and/or atmospheric pressure such that as the user's inhalation force increases, the pressure differential drops to maintain a relatively constant flow rate within the conduit that stays in a desired flow rate range. In some embodiments, the pressure differential increases in a linear relationship with the flow rate as the user's inhalation force increases. Sensory feedback provided by sensors and/or indicator mechanisms, such as those described above, may allow the user to relate inspiratory pressure with the required flow rate required to operate the aerosol generator. Restrictor plate 500 defines a plurality of apertures 502 for air to pass through. Apertures 502 can be positioned around an outer periphery of the restrictor plate 500 such that air passing through the apertures forms a relatively laminar flow downstream of the restrictor plate 500. Apertures 502 can be of any shape or size to create a relatively laminar flow. For example, apertures may be circular and have diameters ranging between about 0.5 mm to 1.5 mm. The size and pattern of the plurality of apertures 502 can prevent airflow through a solid center portion of the restrictor plate 500, while allowing airflow through the apertures on the periphery thereof.

Figure 6:
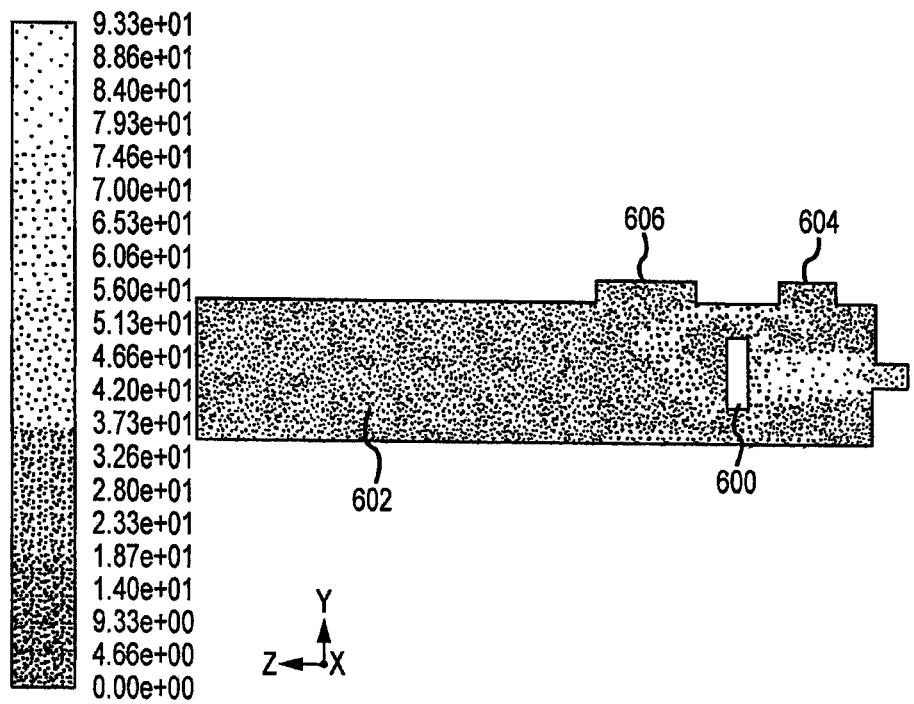
FIG. 6 shows a restrictor plate within a conduit of an aerosolization device according to embodiments of the invention.

FIG. 6 illustrates a restrictor plate 600 positioned within a conduit 602 in accordance with embodiments of the invention. Restrictor plate 600 is disposed within the conduit between a pressure transducer 604 that is in fluid communication with an interior of the conduit and an aerosol generator 606. The pressure transducer 604 monitors a pressure differential within the conduit 602 relative to outside of the conduit and/or atmospheric pressure. A processing unit or IC, such as IC 138 of FIG. 1, may execute software that converts the pressure reading to a flow rate throughout the conduit 602. This flow rate may be used to determine when to activate the aerosol generator 606 to aerosolize a volume of liquid medicament. Restrictor plate 600 may have the characteristics of the restrictor plate 500 discussed above. Restrictor plate 600 creates a laminar flow upstream of the aerosol generator 606 such that the aerosolized medicament is deposited within the laminar flow and entrained within the laminar flow before the aerosolized medicament contacts a wall of the conduit 602 opposite of the aerosol generator 606, in order to maximize the amount of medicament delivered to the user.

Figure 7:
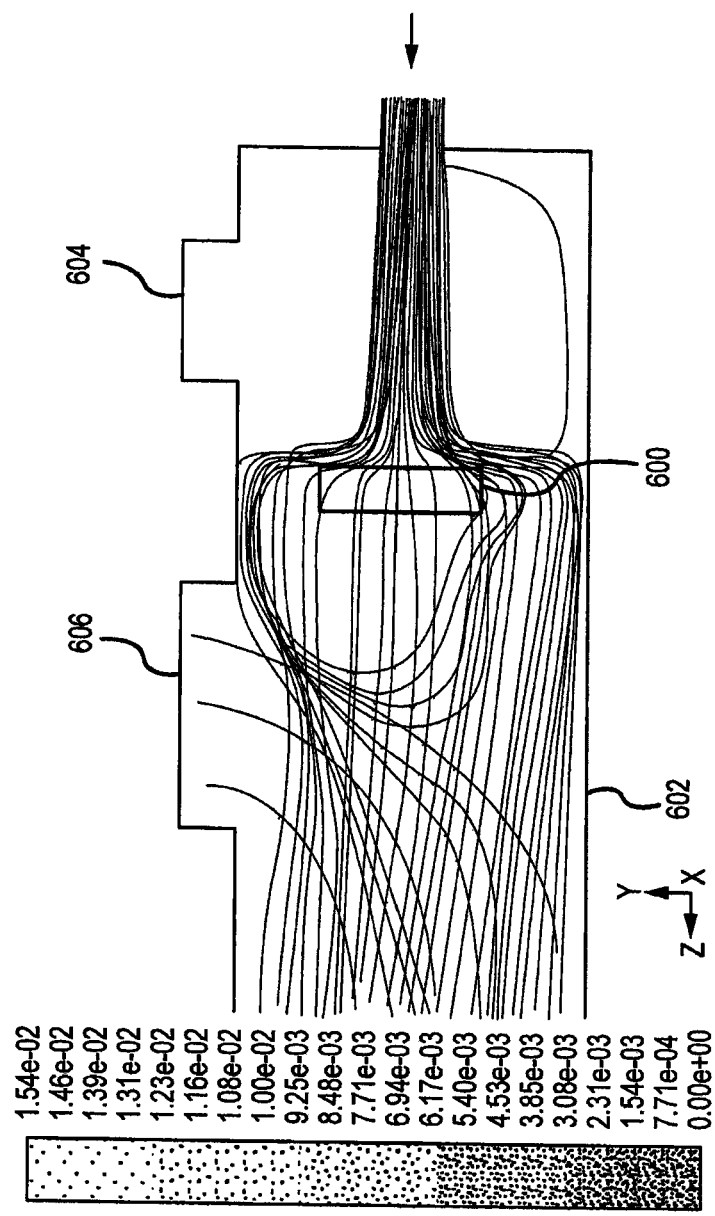
FIG. 7 shows laminar flow created by a restrictor plate within the conduit of FIG. 6 according to embodiments of the invention

FIG. 7 is a laminar flow diagrams of airflow through conduit 602 and restrictor plate 600 having a structure similar to restrictor plate 500. As airflow reaches restrictor plate 600, the pressure differential is increased and a relatively laminar flow is created to contact aerosolized medicament. The laminar flow provides a consistent velocity field to deliver the aerosolized particles to the user's respiratory system in a consistent manner while minimizing impactive losses. Additionally, the laminar flow minimizes an amount of aerosolized medicament that may be deposited on a wall of the conduit. The aerosolized medicament is entrained in the laminar flow before the medicament contacts a wall opposite of the aerosol generator 606. The entrained aerosolized medicament is then carried out of the conduit 602 to a user's respiratory system.

Figure 8A:
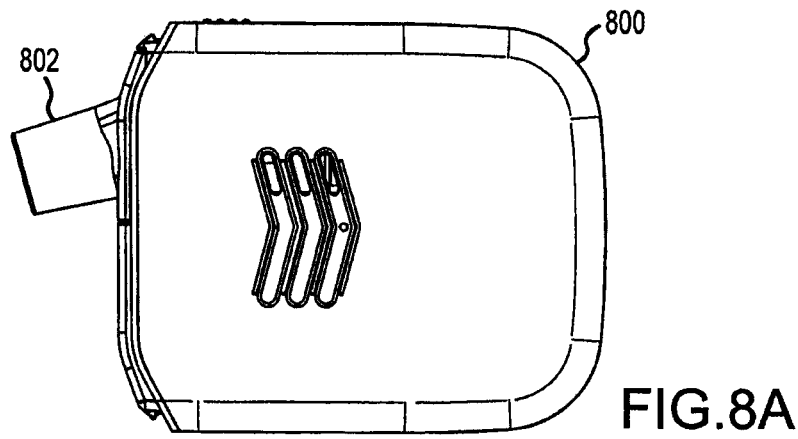
FIGS. 8A-8C depict conduits having mouthpiece ends at various angles according to embodiments of the invention.
Figure 8B:
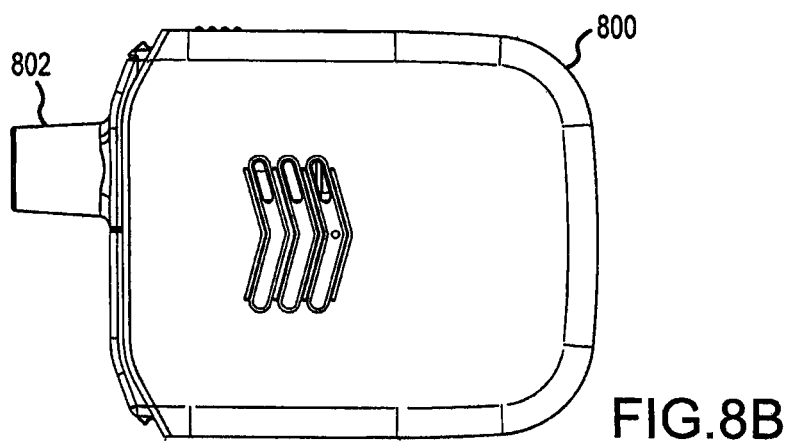
Figure 8C:
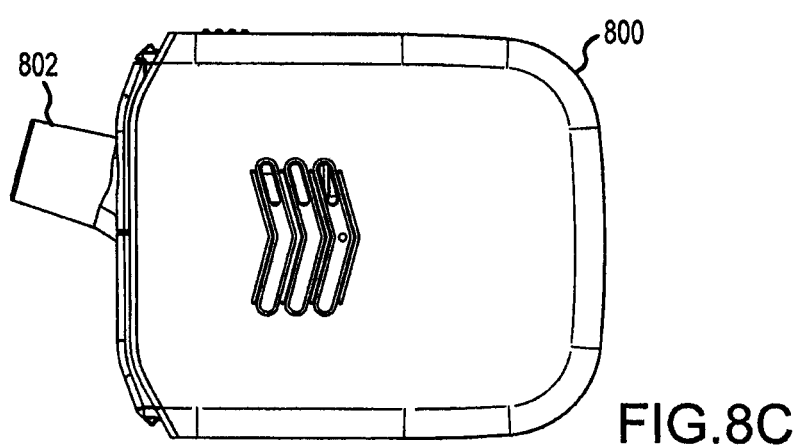

FIGS. 8A-8C show an aerosolization device having a mouthpiece end angled at various angles to direct airflow into a user's respiratory system. Mouthpiece end angles may be set based on the volume of a dose, type of medicament to be delivered, and length and diameter of the conduit of an aerosolization device. FIG. 8A shows an aerosolization device 800 having a mouthpiece end 802 angled downward 15° relative to a horizontal plane. FIG. 8B shows aerosolization device 800 having mouthpiece end 802 parallel relative to a horizontal plane. FIG. 8C shows aerosolization device 800 having mouthpiece end 802 angled upward 15° relative to a horizontal plane. Other angles relative to a horizontal plane of up to 30° up or down relative to a horizontal plane may be used to maximize delivery of the medicament to the user's respiratory system.

Figure 9:
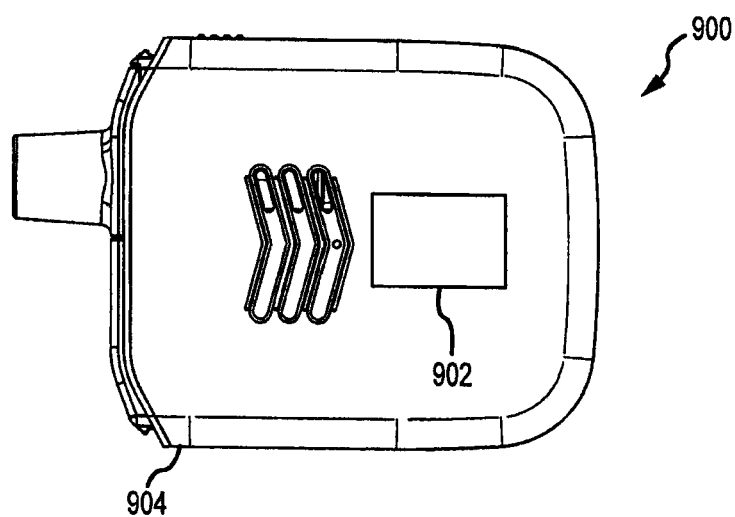
FIG. 9 shows an input device on an aerosolization device according to embodiments of the invention.

FIG. 9 shows an aerosolization device 900 having an input device 902 coupled with a housing 904. In some embodiments, input device 902 may be coupled with a conduit. Input device 902 is configured to receive an input from a user that sets parameters for an inspiratory flow determined by a pressure transducer (not shown) within the conduit. The input may be manually entered by a user, provided via wireless interface, provided via wired interface, such as universal serial bus (USB), or in any other manner. The parameters, which may include a flow rate, an inspiratory pressure, an inspiratory time, and the like, may be used to determine when an aerosol generator of the aerosolization device 900 are actuated, as well as to set ranges for indicator mechanisms (not shown) that direct the user on when and how to breath. An input device 902 may include a keyboard or similar interface, a barcode scanner or RFID reader to receive flow parameters from a user or a container or label of the medicament. Aerosolization device 900 may be configured similar to any of the aerosolization devices described herein, and may include the same or similar features.

Figure 10:
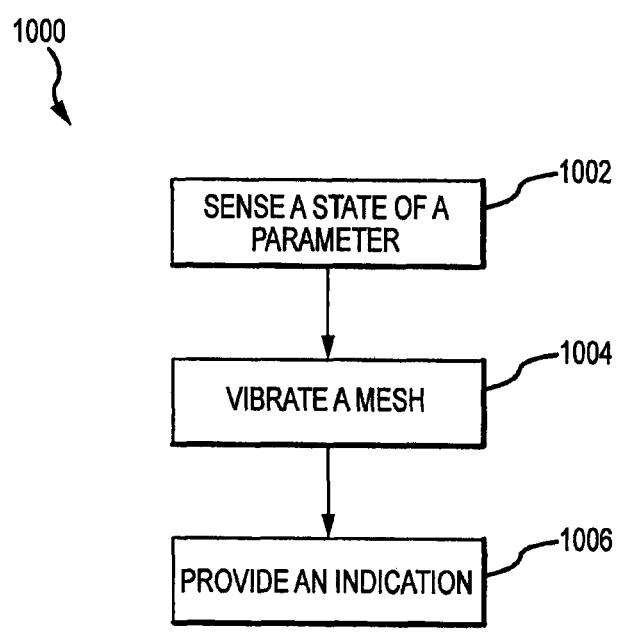
FIG. 10 is a block diagram of a method of using an aerosolization device according to embodiments of the invention.

FIG. 10 depicts a method 1000 of delivering an aerosolized medication to a user's respiratory system using the aerosolization devices described herein. The method may include sensing a state of a flow parameter of an inspiratory flow within a conduit at block 1002. Sensing a state of a flow parameter may be done using sensors, such as a flow sensor or the pressure transducer 404 of FIG. 4. The method may also include vibrating a mesh of an aerosol generator in communication with the conduit to aerosolize a volume of a liquid medicament at block 1004. This vibration produces a plume of aerosolized medicament within a conduit of the aerosolization device when a state of the flow parameter is within a predefined desired range. For example, when an inspiratory flow rate determined by the pressure transducer is within an operating range of the aerosolization device, the mesh may be vibrated. The plume of aerosolized medicament may be provided within a relatively laminar flow produced by a restrictor plate disposed within the conduit upstream of the plume of aerosolized medicament. The laminar flow sweeps the aerosolized medicament toward a mouthpiece end of the conduit before the medicament contacts a wall of the conduit opposite the aerosol generator. The aerosolized medicament is then directed into a user's respiratory system.

In some embodiments, the method may further include providing an indication using an indicator mechanism coupled with the conduit of the state of the flow parameter relative to the predefined desired range at block 1006. In some embodiments, the method may further include providing an indication that the liquid medicament is ready to be aerosolized and providing an indication that substantially all of the liquid medicament has been aerosolized. The method may optionally include receiving an input via an input device of the aerosolization device to set the predefined desired range of the flow parameter. In some embodiments, the method may further include moving a cover that is coupled with the conduit to expose the chamber and vibratable mesh for receiving the liquid medicament. In some embodiments, the method may optionally include receiving a tip of a dispenser within the aerosol generator and receiving a volume of liquid medicament from the dispenser on the mesh. The tip may be maintained a distance above the mesh such that an outer surface of the tip does not contact the received volume of liquid medicament. In some embodiments, the method may also include attaching the conduit and aerosol generator to a housing. For example, the conduit and aerosol generator may be slid into and secured within an opening the housing.

EXPERIMENTAL EXAMPLE

Prevention of contamination due to a user coughing or sneezing into the conduit using an aerosolization device having a vibratable mesh that is laterally offset from an inner wall of the conduit as described in FIGS. 1A and 1B, was simulated by spraying culture broth of five types of pathogens into the conduit using a 100 µl nasal spray pump. One spray was emitted from the primed nasal pump directly into an opening of the conduit. A 30 µl dose of saline was then nebulized using the aerosol generator to simulate the completion of a dose. The aerosolized saline was collected on a culture plate with medium specific to the pathogen testes. The contaminated aerosolization device was then allowed to sit in ambient conditions for 4 hours. Another dose of saline was then nebulized in the aerosolization device with the aerosolized saline again collected on a culture plate. All plates were incubated, with no pathogens found in the saline samples from either sample time.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. An aerosolization device for providing aerosolized medicament to a user, the aerosolization device comprising:
   a conduit having an inner wall that defines an interior of the conduit and a mouthpiece end by which a user may cause an inspiratory flow through the conduit;
   at least one sensor that is in fluid communication with the conduit, the at least one sensor being configured to sense a state of one or more flow parameters of the inspiratory flow;
   at least one indicator mechanism that indicates to a user the state of at least one of the one or more flow parameters relative to a predefined desired range and that also provides an end of dose indicator to indicate that substantially all of a dose of medicament has been delivered, wherein the end of dose indicator is delayed for a period after substantially all of the dose has been delivered;
   an aerosol generator in communication with the conduit and comprising a vibratable mesh, the vibratable mesh laterally offset from the inner wall and outside of the interior of the conduit such that no portion of the vibratable mesh extends into the interior of the conduit;
   a fluid receiving chamber in communication with the aerosol generator for receiving a volume of a liquid medicament, wherein at least a portion of the fluid receiving chamber is tapered such that substantially all of the liquid medicament is directed onto the vibratable mesh for aerosolization; and
   a restrictor plate disposed within the conduit upstream of the aerosol generator and downstream of the at least one sensor, wherein the restrictor plate extends across an entire opening of the conduit such that all airflow introduced into the conduit upstream of the aerosol generator passes through the restrictor plate, wherein the restrictor defines a plurality of apertures, the plurality of apertures being configured to:
      provide an increase in pressure differential that varies with an inspiratory flow rate within the conduit; and
      provide a relatively laminar flow downstream of the restrictor plate compared to upstream of the restrictor plate; and
   wherein the aerosol generator is configured to aerosolize at least a portion of the volume of the liquid medicament only when the one or more flow parameters of the inspiratory flow are within the predefined desired range.

2. The aerosolization device for providing aerosolized medicament to a user according to claim 1, wherein:
   one or both of the conduit and the aerosol generator are attachable to a housing.

3. The aerosolization device for providing aerosolized medicament to a user according to claim 1, wherein:
   the vibratable mesh defines at least 500 apertures, each aperture having a diameter ranging between about 1 to 8 µm.

4. The aerosolization device for providing aerosolized medicament to a user according to claim 1, wherein:
   the tapered portion of the fluid receiving chamber is sufficiently tapered to direct the liquid medicament onto the vibratable mesh such that only a small volume of liquid medicament remains in the fluid receiving chamber after aerosolization is complete, and the small volume of liquid medicament is between 1 and 15 µL.

5. The aerosolization device for providing aerosolized medicament to a user according to claim 1, the aerosolization device further comprising:
   a cover coupled with the fluid receiving chamber, the cover configured to seal the fluid receiving chamber and vibratable mesh from the environment when in a closed position and to expose the fluid receiving chamber and the vibratable mesh to the environment when in an open position.

6. The aerosolization device for providing aerosolized medicament to a user according to claim 1, wherein the conduit comprises:
   an opening that provides access to the chamber, the opening having a diameter that is smaller than a diameter of a top of the chamber.

7. The aerosolization device for providing aerosolized medicament to a user according to claim 1, wherein:
   the plurality of apertures are disposed along an outer periphery of the restrictor, and wherein the restrictor is configured such that no fluid flows through a portion of the restrictor defined between the plurality of apertures.

8. The aerosolization device for providing aerosolized medicament to a user according to claim 1, wherein:
   the tapered portion of the fluid receiving chamber tapers from a first diameter to a smaller second diameter that is positioned proximate the vibratable mesh.

9. An aerosolization device for providing aerosolized medicament to a user, the aerosolization device comprising:
   a conduit that is attachable to a housing, the conduit having an inner wall that defines an interior of the conduit and a mouthpiece end by which a user may cause an inspiratory flow through the conduit;
   at least one sensor that is in fluid communication with the conduit, the at least one sensor being configured to sense a state of one or more flow parameters of the inspiratory flow;
   at least one indicator mechanism that indicates to a user the state of at least one of the one or more flow parameters relative to a predefined desired range and that also provides an end of dose indicator to indicate that substantially all of a dose of medicament has been delivered, wherein the end of dose indicator is delayed for a period after substantially all of the dose has been delivered;
   an aerosol generator in communication with the conduit and comprising a vibratable mesh, the vibratable mesh being laterally offset from the inner wall and outside of the interior of the conduit by a distance between 1 millimeters (mm) and 6 mm such that no portion of the vibratable mesh extends into an interior of the conduit;
   a restrictor disposed within the conduit upstream of the aerosol generator and downstream of the at least one sensor, wherein the restrictor extends across an entire opening of the conduit such that all airflow introduced into the conduit upstream of the aerosol generator passes through the restrictor, wherein the restrictor defines a plurality of apertures, the plurality of apertures being configured to:
      provide an increase in pressure differential that varies with an inspiratory flow rate within the conduit; and
      provide a relatively laminar flow downstream of the restrictor compared to upstream of the restrictor; and
   a fluid receiving chamber in communication with the aerosol generator for receiving a volume of a liquid medicament, wherein at least a portion of the fluid receiving chamber is tapered such that substantially all of the liquid medicament is directed onto the vibratable mesh for aerosolization,
   wherein the aerosol generator is configured to aerosolize at least a portion of the volume of liquid medicament only when the one or more flow parameters of the inspiratory flow sensed by the at least one sensor are within a predefined desired range.

10. The aerosolization device for providing aerosolized medicament to a user according to claim 9, wherein:
   the conduit is configured to deliver the aerosolized medicament at an angle relative to a horizontal plane.

11. The aerosolization device for providing aerosolized medicament to a user according to claim 9, wherein:
   the vibratable mesh defines at least 500 apertures, each aperture having a diameter ranging between 1 to 8 µm.

12. The aerosolization device for providing aerosolized medicament to a user according to claim 9, wherein:
   the one or more flow parameters comprise an inspiratory flow rate within the conduit; and
   the predefined desired range of the inspiratory flow rate is between 5 and 14 liters per minute (L/min).

13. The aerosolization device for providing aerosolized medicament to a user according to claim 9, wherein:
   the tapered portion of the fluid receiving chamber tapers from a first diameter to a smaller second diameter that is positioned proximate the vibratable mesh.

14. A method of delivering an aerosolized medicament to a user's respiratory system, the method comprising:
   sensing a state of a flow parameter of an inspiratory flow within a conduit using at least one sensor, the conduit having an inner wall that defines an interior of the conduit and a mouthpiece end by which a user may cause the inspiratory flow within the conduit;
   providing an indication of the state of the flow parameter relative to a predefined desired range using an indicator mechanism coupled with the conduit;
   vibrating a mesh of an aerosol generator in communication with the conduit to aerosolize a volume of a liquid medicament to produce a plume of aerosolized medicament within the conduit when the state of the flow parameter is within the predefined desired range, wherein:
      the plume of aerosolized medicament is carried toward the mouthpiece end of the conduit;
      the vibratable mesh is laterally offset from the inner wall and outside of the interior of the conduit such that no portion of the vibratable mesh extends into an interior of the conduit; and
      the plume of aerosolized medicament is provided within a relatively laminar flow produced by a restrictor disposed within the conduit upstream of the plume of aerosolized medicament and downstream of the at least one sensor, wherein the restrictor extends across an entire opening of the conduit such that all airflow introduced into the conduit upstream of the aerosol generator passes through the restrictor; and
   providing an end of dose indicator to indicate that substantially all of a dose of medicament has been delivered, wherein the end of dose indicator is delayed for a period after substantially all of the dose has been delivered.

15. The method for using an aerosol device to deliver a volume of medicament according to claim 14, the method further comprising:
   moving a cover that is coupled with the conduit to expose a chamber and vibratable mesh for receiving the liquid medicament.

16. The method for using an aerosol device to deliver a volume of medicament according to claim 14, the method further comprising:
   attaching the conduit and aerosol generator to a housing.

17. The method for using an aerosol device to deliver a volume of medicament according to claim 14, the method further comprising:

receiving an input to set the predefined desired range of the flow parameter.

18. The method for using an aerosol device to deliver a volume of medicament according to claim 14, wherein:
the restrictor defines a plurality of apertures disposed around an outer periphery of the restrictor; and
the plume of aerosolized medicament is carried toward the mouthpiece end of the conduit by the relatively laminar flow.

* * * * *